United States Patent [19]

Hara et al.

[11] Patent Number: 4,941,092

[45] Date of Patent: * Jul. 10, 1990

[54] SIGNAL PROCESSING METHOD FOR DETERMINING BASE SEQUENCE OF NUCLEIC ACID

[75] Inventors: Makoto Hara; Masakazu Hashiue, both of Kaisei; Kazuyoshi Tanaka, Tokyo, all of Japan

[73] Assignee: Fuji Photo Film Co., Ltd., Kanagawa, Japan

[*] Notice: The portion of the term of this patent subsequent to Jan. 19, 2005 has been disclaimed.

[21] Appl. No.: 866,355

[22] Filed: May 23, 1986

[30] Foreign Application Priority Data

May 23, 1985 [JP] Japan ................................ 60-111185
May 23, 1985 [JP] Japan ................................ 60-111186

[51] Int. Cl.$^5$ ........................ G01N 33/58; C12Q 1/68
[52] U.S. Cl. ........................... 364/413.15; 364/413.01; 435/6; 935/77
[58] Field of Search ................. 364/413.01, 413.15; 382/6; 935/77; 435/6

[56] References Cited

U.S. PATENT DOCUMENTS 4,720,786  1/1988  Hara ............................... 364/413.01

FOREIGN PATENT DOCUMENTS 0155777  8/1984  European Pat. Off. ................ 435/6

Primary Examiner—Michael R. Fleming
Assistant Examiner—Kim Thanh T. Bui
Attorney, Agent, or Firm—Sixbey, Freidman, Leedom & Ferguson

[57] ABSTRACT

A signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in one-dimensional direction on a support medium, which comprises steps of:

(1) detecting at least two bands continuously in the lower part of each resolved row and numbering the bands consecutively in order from the lower end;

(2) obtaining correlation of a distance between the detected bands in the resolving direction with the band's number and predicting positions of undetected bands in the resolving direction from the correlation;

(3) detecting at least one band on the resolved rows on the basis of the predicted positions and numbering the bands consecutively;

(4) obtaining the correlation of the distance between the bands with the band's number for the already detected bands including the band newly detected in the step (3), and predicting positions of undetected bands from the correlation; and (5) repeating in order the steps (3) and (4) to thereby detect all bands on the resolved rows.

31 Claims, 3 Drawing Sheets

SIGNAL PROCESSING METHOD FOR DETERMINING BASE SEQUENCE OF NUCLEIC ACID

BACKGROUND OF THE INVENTION

1. Field of the Invention

This invention relates to a signal processing method for determining base sequence of nucleic acids.

2. Description of the Prior Art

It is essential to obtain genetic information carried by organisms in order to make the function or replicated mechanism of the organism clear in the field of molecular biology which has been rapidly developed in recent years. Particularly, it is essential to determine base sequence of nucleic acids such as DNA (or DNA fragment; the same applies hereinbelow) which carries specific genetic information.

Maxam-Gilbert method and Sanger-Coulson method are known as typical methods for determining the base sequence of nucleic acids such as DNA and RNA. In the former Maxam-Gilbert method, a group containing a radioactive isotope such as $^{32}P$ is attached to a chain molecule of DNA or a DNA fragment at one end to label it with the radioactive element and then the bond between the constitutional units of the chain molecule is base-specifically cleaved by a chemical reaction. A mixture of the resulting base-specific DNA cleavage products is resolved through gel electrophoresis to obtain a resolved pattern (not visible) wherein each of the numerous cleavage products is resolved on the gel support medium. The resolved pattern is visualized on a radiographic film such as an X-ray film to obtain an autoradiograph thereof as a visible image. The bases in certain positional relationships with the end of the radioactive element-attached chain molecule can be sequentially determined according to the visualized autoradiograph and the applied base-specific cleavage means. In this way, the sequence for all bases of the DNA specimen can be determined.

In the latter Sanger-Coulson method, synthetic DNA products which are complementary to the chain molecule of DNA or DNA fragment and radioactively labeled, are base-specifically synthesized by utilizing a chemical reaction, and the obtained mixture of numerous synthetic DNA products is resolved on a support medium by gel electrophoresis to obtain a resolved pattern. In a similar manner to that described above, the base sequence of DNA can be determined according to the visualized autoradiograph.

For the purpose of carrying out the determination of the base sequence of nucleic acids simply with high accuracy in autoradiography, there are described in U.S. Pat. No. 549,417 and U.S. Application Ser. No. 664,405 autoradiographic procedures which utilize a radiation image recording and reproducing method using a stimulable phosphor sheet, in place of conventional radiography using a radiosensitive material such as an X-ray film. The stimulable phosphor sheet comprises a stimulable phosphor and has such properties that when exposed to a radiation, the stimulable phosphor absorbs a portion of radiation energy and then emits light (stimulated emission) corresponding to the radiation energy stored therein upon excitation with an electromagnetic wave (stimulating rays) such as visible light or infrared rays. According to this method, exposure time can be greatly shortened and there is no fear of causing problems such as chemical fog associated with prior arts. Further, since the autoradiograph having information on radioactively labeled substances is stored in the phosphor sheet as radiation energy and then read out as stimulated emission in time sequence, information can be expressed by the form of numerals and/or symbols in addition to image.

The base sequence of the nucleic acids has been conventionally determined by visually judging individual resolved positions of the base-specific cleavage products or the base-specific synthetic products of radioactively labeled nucleic acid (hereinafter simply referred to as base-specific fragments of nucleic acid) on the autoradiograph and comparing them among the resolved rows thereof. Namely, the analysis of the autoradiograph is done by observing the visualized autoradiograph with eyes, and such visual analysis requires great amounts of time and labor.

Further, since the visual analysis of the autoradiograph varies or fluctuates owing to the skill of investigators, the results on the determination of the base sequence of nucleic acid vary depending on the investigators and the accuracy of information is limited to a certain extent.

In order to improve the accuracy of the information, there are proposed in U.S. Application Ser. Nos. 568,877 and 730,034 methods for automatically determining the base sequence of DNA by obtaining the autoradiograph as digital signals and subjecting the digital signals to appropriate signal processing. The digital signals corresponding to the autoradiograph of the radioactively labeled substances can be obtained either by visualizing the autoradiograph on a radiographic film and photoelectrically reading out the visible image on said film by means of reflected light or transmitted light when the conventional radiography is employed, or by directly reading out the stimulable phosphor sheet without the visualization of the autoradiograph when the radiation image recording and reproducing method is employed.

However, the resolved pattern obtained by resolving (developing) radioactively labeled substances on a support medium by electrophoresis or the like is liable to cause various distortion and noise. For instance, the noises are caused by that radiosensitive materials are exposed to a radiation radiating from radioactive impurities incorporated in the support medium or natural radioactivity, or that its radiation energy is absorbed by the stimulable phosphor sheet and stored therein. It is highly desired that the base sequence of the nucleic acids can be automatically determined with high accuracy by subjecting the digital signals corresponding to the autoradiograph to signal processing even when such noises are caused.

Generally, the resolved pattern has such a band distribution that the spaces between the resolved bands are sparse in the lower part (region where resolved distance is long) and the spaces therebetween become denser toward the upper resolution-starting position. The term "lower part" used herein means a region below nearly the middle of the support medium, while the term "upper part" used herein means a region above it. In the upper part, the separation of the bands is insufficient so that two or three bands are sometimes combined together and as a results, one wider band will be unfavorably formed. Even when the resolved pattern has such combined (fused) bands, it is highly desired to obtain more information on the base sequence of the nucleic acids by one measurement with high accuracy through the signal processing.

SUMMARY OF THE INVENTION

The present inventor has found that the base sequence of the nucleic acids can be automatically determined with easiness and high accuracy by subjecting digital signals corresponding to the autoradiograph of the resolved pattern containing combined bands in the method for the automatic determination of the base sequence of nucleic acids by using autoradiography.

The present invention provides a signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in one-dimensional direction on a support medium, which comprises steps of:

(1) detecting at least two bands continuously in the lower part of each resolved row and numbering the bands consecutively in order from the lower end;

(2) obtaining correlation of a distance between the detected bands in the resolving direction with the band's number and predicting positions of undetected bands in the resolving direction from the correlation;

(3) detecting at least one band on the resolved rows on the basis of the predicted positions and numbering the band consecutively;

(4) obtaining the correlation of the distance between the bands with the band's number for the already detected bands including the band newly detected in the step (3), and predicting positions of undetected bands from the correlation; and (5) repeating in order the steps (3) and (4) to thereby detect all bands on the resolved rows.

The present invention also provides a signal processing method for determining the base sequence of nucleic acids by subjecting said digital signals corresponding to an autoradiograph to signal processing, which comprises steps of:

(1) detecting at least two bands continuously in the lower part of each resolved row and numbering the bands consecutively in order from the lower end;

(2) obtaining correlation between a resolved distance of the detected band and the band's number and predicting positions of undetected bands in the resolving direction from the correlation;

(3) detecting at least one band on the resolved rows on the basis of the predicted positions and numbering the band consecutively;

(4) obtaining the correlation of the resolved distance of the band and the band's number for the already detected bands including the band newly detected in the step (3), and predicting positions of undetected bands from the correlation; and (5) repeating in order the steps (3) and (4) to thereby detect all bands on the resolved rows.

The present invention further provides a signal processing method for determining the base sequence of nucleic acids by subjecting said digital signals corresponding to an autoradiograph to signal processing, which comprises steps of:

(1) detecting at least two bands continuously in the lower part of each resolved row and numbering the bands consecutively in order from the lower end;

(2) obtaining correlation of a distance between the detected bands in the resolving direction with the band's number and predicting positions of undetected bands in the resolving direction from the correlation; and (3) detecting all bands on the resolved rows on the basis of the predicted positions.

According to the present invention, the base sequence of the nucleic acids can be simply determined with high accuracy by processing the digital signals corresponding to the autoradiograph of the resolved pattern which is obtained by resolving a mixture of the base-specific specific fragments of a nucleic acid on a support medium, through an appropriate signal processing circuit having a function capable of separating combined bands into individual ones, even when the separation of bands in the pattern is insufficient and the bands are partially combined together. Further, the combined bands which are hardly separated by conventional methods can be separated from each other by the method of the present invention, and hence, an amount of information on the base sequence of the nucleic acids obtained by one autoradiographic measurement is increased and the determination of the base sequence of the nucleic acids can be more facilitated.

The present inventors have found out that the sequence of bands can be easily determined in the lower region of the resolved pattern, since the bands in the lower region are definitely separated from one another, unlike the bands in the upper region. The method for separating properly and simply the combined bands according to the present invention is based on this finding. More in detail, in the lower region of the resolved pattern, the sequence of the bands can be easily determined and the space between the bands (or the resolved distance of the band) is definitely correlative to the consecutive band's number. Positions at which bands should exist can be concluded by predicting the space between the bands (or the resolved distance thereof) in the more upper region from this correlation, and the combined bands can be separated from one another even when a plurality of bands are combined together.

In the first and second methods according to the present invention, the correlation between the bands' space (instead of which, the resolved distance of band is employed in the second method) and the band's number is sectionally obtained to detect bands successively on the basis of the correlations. In the third method according to the invention, the correlation between the bands' space and the band's number is once obtained to detect bands en bloc on the basis of the correlation.

Particularly, the correlation between the bands' space (or the resolved distance) and the consecutive band's number can be locally represented by a straight line, so that the correlation therebetween can be approximated by a straight line and easily determined when the number of bands employed therefor are not so large.

In this way, the base sequence of the nucleic acids can be simply determined with high accuracy, since the sequence of bands is determined while carrying out the separation of combined bands.

DETAILED DESCRIPTION OF THE INVENTION

Figure 1:
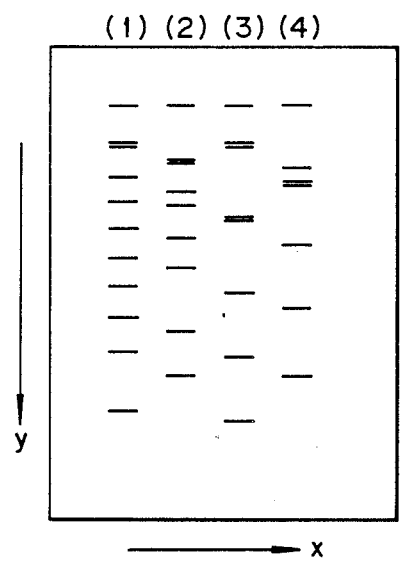
FIG. 1 shows an example of an electrophoretic pattern in which combined bands are appeared.

Examples of samples employable in the present invention include mixtures of base-specific fragments of nucleic acids such as DNA and RNA labeled with a radioactive element. The term "fragments" of nucleic acids mean portions of a long-chain molecule. For instance, a mixture of base-specific DNA cleavage products, which is a kind of a mixture of base-specific DNA fragments, can be obtained by base-specifically cleaving the radioactively labeled DNA according to the aforementioned Maxam-Gilbert method. A mixture of base-specific DNA synthetic products can be obtained by synthesizing from radioactively labeled deoxynucleoside triphosphates and DNA polymerase by use of DNA as a template according to the aforementioned Sanger-Coulson method.

Mixtures of base-specific RNA fragments can be also obtained as a mixture of cleavage products or a mixture of synthetic products in the similar manner to the above-described methods. DNA is composed of four kinds of bases: adenine, guanine, thymine and cytosine as its constitutional units, and RNA is composed of four kinds of bases: adenine, guanine, uracil and cytosine.

These substances can be labeled with a radioactive element such as $^{32}P$, $^{14}C$, $^{36}S$, $^{3}H$ or $^{125}I$ by any of appropriate methods.

A sample, which is a mixture of the base-specific fragments of a nucleic acid labeled with a radioactive element, can be resolved (developed) on a known support medium such as a gel support medium by any of conventional resolving (developing) procedures such as electrophoresis, thin layer chromatography, column chromatography and paper chromatography.

The support medium on which the radioactively labeled substances are resolved, is autoradiographed to obtain an autoradiograph thereof by means of the conventional radiography using a radiosensitive material or the radiation image recording and reproducing method using a stimulable phosphor sheet. The digital signals corresponding to the autoradiograph can be then obtained through an appropriate read-out system.

When the conventional radiography is used, the support medium and a radiosensitive material such as a X-ray film are placed together in layers at a low temperature or room temperature for a long period of time (several hours to several tens of hours) to expose the radiographic film. The radiographic film is then developed to visualize the autoradiograph of the radioactively labeled substances on the film, and the visualized autoradiograph is read out by using an image read-out system. For instance, the radiographic film is irradiated with a light beam and the light transmitted thereby or reflected therefrom is photoelectrically detected, whereby the autoradiograph can be obtained as electric signals. Further, digital signals corresponding to the electric signals are obtained through A/D conversion.

When the radiation image recording and reproducing method is used, the support medium and the stimulable phosphor sheet are placed together in layers at an ambient temperature for a short period of time (several seconds to several tens of minutes) to store radiation energy radiating from the radioactively labeled substances in the phosphor sheet, whereby the autoradiograph is recorded as a kind of a latent image (energy-stored image) on the phosphor sheet. The stimulable phosphor sheet has a basic structure where a support comprising, for instance, a plastic film, a phosphor layer comprising a stimulable phosphor such as a divalent europium activated barium fluorobromide phosphor (BaFBr:Eu$^{2+}$) and a transparent protective film are laminated in this order. The stimulable phosphor contained in the stimulable phosphor sheet has such characteristics that the phosphor absorbs and stores radiation energy emitted by the labeled substances when irradiated with a radiation such as X-rays and then releases the stored radiation energy as stimulated emission when excited with visible light to infrared rays.

Subsequently, the autoradiograph stored and recorded on the stimulable phosphor sheet is read out by using a read-out system. For instance, the phosphor sheet is scanned with a laser beam to release the radiation energy stored in the stimulable phosphor as light emission and the emitted light is photoelectrically detected, so that the autoradiograph can be directly obtained as electric signals without the visualization of the autoradiograph. Further, digital signals corresponding to the autoradio-graph can be obtained from the electric signals through A/D conversion.

The above-described methods for measuring the auto-radiograph and obtaining the digital signals corresponding thereto are described in more detail in the aforementioned U.S. Pat. No. 549,417 and U.S. Application Ser. No. 568,877.

While the methods for obtaining the digital signals corresponding to the autoradiograph using the conventional radiography and the radiation image recording and reproducing method are described above, the present invention is not limited thereto and digital signals obtained by any other methods can be applied to the signal processing method of the invention, provided that they correspond to the autoradiograph.

In the above read-out procedures, it is not always necessary to conduct the read-out operation of the autoradiograph all over the surface of the radiographic film or the stimulable phosphor sheet. Only the image region may be subjected to the read-out operation.

In the present invention, there may be previously inputted information on the location of each resolved row and the width of band to preset read-out conditions and then conducted scanning at a scanning line density such that each band is traversed by at least one scanning line in the read-out operation, so as to shorten read-out time and obtain efficiently necessary information. The digital signals corresponding to the autoradiograph in the invention also include the thus-obtained digital signals.

The obtained digital signals $D_{xy}$ comprise a coordinate (x,y) which is represented by a coordinate system defined by the radiographic film or the stimulable phosphor sheet and a signal level (z) at the coordinate. The signal level represents the density of image at the coordinate, that is, the amount of the radioactively labeled substances. Accordingly, a series of the digital signals (that is, digital image data) have information on two-dimensional location of the labeled substances.

The thus-obtained digital signals corresponding to the autoradiograph of the radioactively labeled substances resolved on a support medium, is subjected to signal processing to determine the base sequence of nucleic acid according to the invention described in more detail below.

Now, the signal processing method of the present invention will be described with respect to the first and second methods by referring to an example of electrophoretic rows (resolved rows) formed with a combination of the following four groups of base-specific DNA fragments labeled with a radioactive element:
 (1) guanine (G)—specific DNA fragments,
 (2) adenine (A)—specific DNA fragments,
 (3) thymine (T)—specific DNA fragments,
 (4) cytosine (C)—specific DNA fragments.

Each of said base-specific DNA fragments is composed of base-specific cleavage products or synthetic products which have various lengths and the same base at terminals.

FIG. 1 shows an autoradiograph of an electrophoretic pattern in which the above four groups (1) to (4) of the base-specific DNA fragments are electrophoresed into the first to fourth slots, respectively. Spaces between bands are sparse in the lower region of the pattern and the spaces become denser toward the upper region thereof.

Digital signals corresponding to the autoradiograph are temporarily stored in a memory device of the signal processing circuit (that is, a nonvolatile memory unit such as a buffer memory, a magnetic disk, etc.).

In the first place, at least two bands are continuously detected in the lower region of each electrophoretic row (lane) and the sequence thereof is determined.

For instance, digital signals within a given area along each electrophoretic direction are extracted and a one-dimensional waveform composed of position (y) of the extracted signal and signal level (z) at its position is prepared for each lane. The one-dimensional waveforms of the lanes can be directly prepared from the resulting digital signals, when the detection of digital signals is done by scanning the digital image data at such a scanning line density that each band is traversed by a scanning line.

Figure 2:
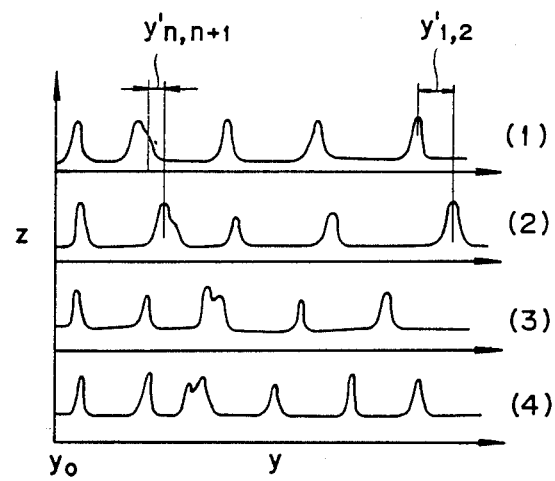
FIG. 2 shows one-dimensional waveforms (1) to (4) composed of signal position (y) and signal level (z) for individual lanes.

FIG. 2 shows one-dimensional waveforms composed of signal position (y) and signal level (z) for the individual lanes, in which the waveforms (1) to (4) correspond to the respective slots of FIG. 1. The position ($y=y_0$) of the ordinate indicates a base point on the digital image data. For instance, the base point is allowed to be the slot position.

In the right-side region (a region where y is large) of each one-dimensional waveform of FIG. 2, positions where signal level is maximum are found out, for example, by searching points where a sign of a difference in signal level is inverted [that is, a plus(+) sign changes to a minus(−) sign]. It is necessary to find out two or more maximum points continuously on each one-dimensional waveform, whereby at least one basic band space for a pattern can be obtained. The positions where the signal level is maximum are allowed to be band positions. The number of bands to be detected varies depending on the total number of bands on the electrophoretic pattern and the pattern profile, but it is preferred to detect tenodd bands to several tens of bands in total, when the total number of bands is in the range of 150 to 200. It is also desirable to detect the bands in the lowermost part of the pattern. These bands are allowed to be initial data for predicting the positions of subsequent bands.

All of the detected bands are consecutively numbered (n) in order by starting the numbering from the band at a position (y) which is the farthest one from the base point. The sequence of the bands is easily determined in the lower region of the pattern, since the spaces between the bands are sparse and the bands are definitely separated from each other, as is apparent from FIG. 1.

In the second place, correlation of a distance between bands in the electrophoretic direction, namely a space therebetween (referred to as "pitch"), with the band's number is determined from the initial data, and the positions of bands to be subsequently detected are predicted on the basis of the correlation.

Figure 3:
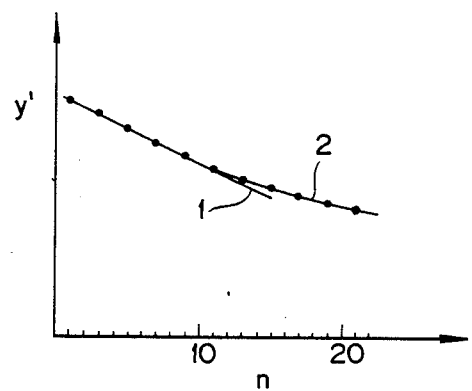
FIG. 3 shows correlations between band's number (n) and electrophoretic pitch (y') for every lane, wherein Line 1 is a sectional regression line for initial data and Curve 2 is a regression curve.

A graph wherein the band's number (n) is plotted as abscissa and the electrophoretic pitch (y') as ordinate is prepared to obtain a regression line (straight line) such as Line 1 in FIG. 3. In FIG. 3, Line 1 is a regression line composed of the band's number (n) and the electrophoretic pitch (y'). For instance, the electrophoretic pitch $y'_{1,2}$ for the first band (n=1) represents a distance between the first band and the second band ($y'_{1,2}=y_1-y_2$)

The regression line can be represented by the following formula:

$$y'=an+b$$

wherein a and b are each a constant.

Usually, relationship between the band's number and the electrophoretic pitch is locally linear in the lower region of the electrophoretic pattern and the correlation therebetween is approximated by a regression line as shown by Line 1 in FIG. 3. The correlation between the band's number and the pitch is by no means limited to the above regression line but the correlation therebetween can be represented by other regression mode. For example, it may be approximated by a curve of higher-order to obtain a regression curve, whereby the correlation can be determined with higher accuracy.

For instance, the regression line in FIG. 3 is extrapolated toward the direction of increasing n, and thereby, a space ($y'_{n,n+1}$) between the detected band having the greatest number and the next band to be detected is obtained. It can be predicted that a position ($y_{n+1}$) of the next band to be detected is $y_n-y'_{n,n+1}$.

Alternatively, a migration distance of each band may be employed in place of the electrophoretic pitch. Correlation between the migration distance of a band and the band's number is similar to the above-mentioned correlation and represented by a regression line such as Line 1 in FIG. 3. In this case, the migration distance of the next band to be detected can be directly determined by extrapolating the regression line toward the direction of increasing n. Namely, the next band is predicted.

In the third place, at least one band on the electrophoretic pattern is detected on the basis of the predicted positions and consecutively numbered.

Among the lanes, there is found out a lane having a signal of the higher level within a given range ($y_{n+1}\pm\alpha$, wherein $\alpha$ is a search interval) from the predicted position on the waveforms (1) to (4) of FIG. 2, and it is decided that a band is to exist on said lane. When a signal of the maximum level is found out within the range, the new band is decided to be at the position of the maximum level, or when a signal of the maximum level is not found out, the predicted position is decided to be the position of the next band.

That is, it can be estimated that a band exists at the predicted position on the lane having the signal of the highest level, even when the maximum level is not found out within a given range from the predicted position on the one-dimensional waveforms because of two or more bands being combined together. It is preferred that the intensities (signal levels) of the one-dimensional waveforms are previously controlled to be at an appropriate level through signal processing, when signal levels of the lanes considerably vary from one another due to a difference in the amount of the sample to be introduced into each slot.

Alternatively, a given threshold value is preset and a lane having a signal of level not less than said threshold is found out, to decide that a band is to exist on said lane. The threshold value may be preset for every lane. When two or more lanes have the signal of such level, a lane having the signal of the highest one is chosen by comparing them, since the combination of the four groups of base-specific DNA fragments is exclusive and there is no possibility that one band (of the same fragment) exists simultaneously on two or more lanes.

In the fourth place, the newly detected band(s) is added to the already detected bands, and the correlation (regression line or regression curve) between the electrophoretic pitch (or migration distance) and the band's number is again determined for these bands. For example, the data ($y'_{n,n+1}$) of the n+1-th band is added to the initial data for the prediction, and the correlation is determined from the data of the first to the n+1-th bands.

In the same manner as described above, a position of the next band to be detected is predicted on the basis of the resulting regression line or curve (see, Curve 2 in FIG. 3), and a band on the pattern is newly detected on the basis of the predicted position. Thus, the operation is repeatedly made, in which every time a band is detected on the basis of the predicted position, the correlation between the pitch (or migration distance) and the band's number is modified and a position of the next band is predicted, whereby all of bands to be allowed to appear on the pattern can be detected on any of the lanes.

The operation can be simplified by carrying out the detection of band on the basis of the predicted position at rate of a fixed unit. Preferably, the number of bands to be detected by one operation is half or less of the number of the bands used as the initial data, and for instance, the detection unit consists of 5 to 10 bands. In this way, the regression line or curve can be applied to individual sections into which the lanes are divided.

Every time the operation is made, the amount of the band data to be used for determining the correlation is more and more increased. Thus, as the operation is repeatedly made, the correlation between the pitch (or migration distance) and the band's number is no longer linear and will be represented by a regression curve obtained by approximating with an appropriate curve (e.g., a polynomial expression or exponential function) by means of a method of least squares (see, Curve 2 in FIG. 3).

In modifying the correlation between the pitch (or migration distance) and the band's number, the newly detected band(s) is added to the already detected bands and instead the band(s) having the lowest band's number is excluded therefrom, and the correlation for these bands may be determined. In this case, the amount of the band data to be used for the determination of the correlation is always constant, so that the correlation can be represented by a nearly fixed relation such as a straight line (see, Line 2 in FIG. 4) even when the operation is repeated. Since the correlation between the pitch (or migration distance) and the band's number is locally linear, it is possible that the correlation is always obtained by approximating with a simple linear function through the repeated operations and the signal processing is further simplified.

Figure 4:
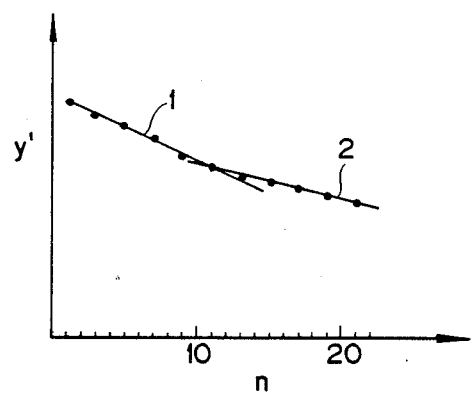
FIG. 4 shows correlations between band's number (n) and electrophoretic pitch (y') for every lane, wherein Lines 1 and 2 are sectional regression lines, respectively.

In FIG. 4, Line 1 is a regression line for the initial data and Line 2 is another regression line for the band data including the newly detected band(s) and excluding the band(s) having the lower number among the initial data instead.

The detection order of the thus-obtained bands means the base sequence of DNA. Since the slots (1) to (4) have information on the terminal bases of (G), (A), (T) and (C), respectively, the base sequence of DNA can be obtained by substituting the base corresponding to a slot to which each band belongs for the bands. For instance, the following base sequence of DNA can be obtained.

A—G—C—T—C—A—G— . . .

When the electrophoretic pattern causes a smiling phenomenon, correction for the smiling phenomenon may be made before the digital signals are subjected to the above-described signal processing.

The smiling phenomenon is a phenomenon in which the migration distances of the radioactively labeled substances at the both sides of the support medium are shorter than that in the vicinity of the center thereof. The smiling phenomenon is caused by heat dissipation effect (so-called edge effect) during the electrophoresis.

The smiling phenomenon can be corrected in the following manner.

In the electrophoretic pattern which causes the smiling phenomenon, bands (the shape of which is rectangle extending perpendicularly to the electrophoretic direction) is not strictly perpendicular (horizontal) to the electrophoretic direction but inclined according to the degree of the smiling effect. Therefore, the inclination of at least one band for each lane is detected. For instance, the inclination can be determined from a regression line, which is obtained by scanning the digital image data at such a scanning line density that each band is traversed by at least two scanning lines to extract digital signals, preparing a one-dimensional waveform for each scanning line, and then joining positions at maximum signal level on the waveforms to one another. Alternatively, the digital signals to be extracted may be directly obtained in the course of the read-out operation of the autoradiograph.

Subsequently, a band (standard band) on a lane (which is allowed to be a standard lane) which exhibits the smallest smiling effect is extrapolated on lanes other than the standard lane on the basis of the inclination thereof and the inclination of the nearest bands on the other lanes, to determine the relative positions of the standard band on the other lanes. The ratios of the migration distance for the other lanes are determined from the position of the standard band and the relative positions thereof. The resulting ratios mean the degree of the smiling effect of the individual lanes against the standard lane. The migration distance of each lane is extended or shortened in the lump on the basis of said ratio. In this way, the smiling effect can be corrected for all lanes.

The methods for the smiling correction are described in more detail in our co-pending Japanese Patent Application No. 60(1985)-74899.

When the electrophoretic pattern causes offset distortion, correction for the offset distortion may be made before the digital signals are subjected to the above-described signal processing.

The offset distortion means deviation of position of the whole lanes from one another, caused by a difference between the slots in the electrophoresis-starting position or time of samples. The offset distortion is caused, for instance, by that the shapes (size of recess) of slots (inlet of sample) provided at the upper end of a gel medium are uneven and different from one another; that positions on which a sample is deposited are deviated from one another in introducing the sample into the gel medium; or that urea is not completely washed out of the gel medium just before the sample is introduced and as a result, the sample penetrates into the gel medium at different rates.

The correction for the offset distortion can be made in the following manner.

In the lower region of the electrophoretic pattern, the spaces between the bands are generally sparse as shown in FIG. 1. At least two bands on each lane are detected and the detected bands are consecutively numbered in order from the lower end of the pattern. This operation can be substituted by the initial band-detecting operation in the afore-described signal processing for the separation of the combined bands.

Subsequently, correlation (e.g., regression line) between the band's number and the migration distance thereof is determined, a difference in the migration distance between lanes is determined on the basis of the correlation, and the migration positions of the individual lanes (that is, one-dimensional waveforms of the lanes) are wholly shifted by taking the difference as the locational deviation of the lanes from one another. In this way, the correction for the offset distortion on all lanes can be made en bloc.

The locational deviation of the lanes from one another is not always uniform over the whole of the lanes. Accordingly, the correction for the offset distortion can be alternatively made by repeating the operation comprising determining the correlation between the band's number and the migration distance for a given section and then correcting the deviation of positions in the next section on the basis of the correlation. However, it is necessary that the correlation must be determined in regions where the combined bands do not appear. In this case, it is possible that the separation of the combined bands is done while correcting the offset distortion, when the separation of the combined bands is sectionally conducted in a unit of plural bands.

The correction for the offset distortion through signal processing is described in more detail in our copending Japanese Patent Applications No. 60(1985)-85275 and 60(1985)-85276.

In the method of the present invention, both of the smiling correction and the offset-distortion correction can be made and the correction may be made in any order.

The signal processing method according to the present invention will be described with respect to the third method by referring to the above-mentioned example.

Firstly, at least two bands on each lane are continuously detected and the sequence thereof is determined in the same manner as described above.

Secondly, the correlation between the electrophoretic pitch and the band's number is determined for the detected bands, and the positions of other bands to be detected are predicted from the correlation.

Figure 5:
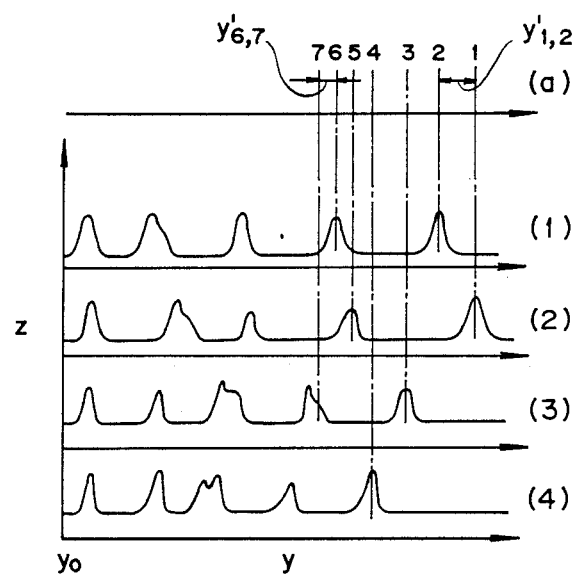
FIG. 5 shows one-dimensional waveforms (1) to (4) composed of signal position (y) and signal level (z) for individual lanes and a sequence of bands (a).

In FIG. 5, (1) to (4) are one-dimensional waveforms composed of signal positions (y) and signal levels (z), and (a) indicates sequence of bands, which correspond to the respective slots of FIG. 1. The electrophoretic pitch between the first band and the second band, for example, is represented by $y'_{1,2}$.

The pitches between the two continuous bands are individually calculated and the correlation thereof with the band's number is obtained. The correlation can be represented by the functional formula:

$$y'_{n,n+1} = f(n+1)$$

The correlation is concretely obtained as a linear equation or an equation of higher-order.

The positions of undetected bands can be predicted from the resulting correlation. For example, $y_6 - y'_{6,7}$ is predicted for the position ($y_7$) of the seventh band.

Thirdly, all of the bands on the electrophoretic pattern are detected on the basis of these predicted positions.

Points or areas where signal level is not less than a given value (threshold) are searched on the one-dimensional waveform of each lane and then extracted therefrom. When the extracted point (or area) corresponds to (or includes) the predicted band position to be next detected, the next band is decided to exist on the lane having said point (area). For example, the seventh band is decided to exist on the lane of the third slot as shown in FIG. 5.

That is, it can be estimated that a band exists at the predicted position at which signal level is not less than the threshold, even when the maximum level is not found out on the one-dimensional waveforms because of two or more bands being combined together. It is preferred that the intensities (signal levels) of the one-dimensional waveforms are previously controlled to be at an appropriate level through signal processing, when signal levels of the lanes considerably vary from one another due to a difference in the amount of sample to be introduced into each slot.

When there are two or more lanes having the signal of a level not less than the threshold at the predicted position, a lane having the signal of the higher level therebetween is chosen, sine the sample is the exclusive combination of base-specific DNA fragments and there is no possibility that one band (of the same fragment) exists simultaneously on two or more lanes.

In this way, bands are detected one by one from the lower end of the pattern on the basis of the prediction of the band portions and the sequence thereof is determined.

The detection order of the bands means the base sequence of DNA. The DNA sequence is obtained by substituting the band sequence with bases corresponding to slots to which the individual bands belong.

The correction for the smiling phenomenon and/or the offset-distortion can be also made in the third method.

Thus, the base sequence of one chain molecule of DNA can be determined. The representation mode of the information on the base sequence of DNA is by no means limited to the above-mentioned mode, and other representation modes may be utilized optionally. For instance, the intensity (z') of each band can be represented as the relative amount of the radioactively labeled substances, if desired. Further, the base sequence of both two chain molecules of DNA can be also represented.

Information can be also displayed as an image on the basis of the digital signals processed on the separation of combined bands. The positions of the detected bands are displayed together with the original autoradiographic image. In this case, investigators themselves can finally determine the base sequence on the basis of the display image.

In the above-mentioned example, there has been described the case where the exclusive combination of the mixture (G, A, T, C) of the base-specific DNA fragments as a sample is used, but the signal processing method of the present invention is by no means limited to the above combination, and other combinations can be used. For instance, a combination of (G, G+A, T+C, C) can be used. Further, the signal processing method of the present invention can be also applied to the mixtures (for instance, a combination of G, A, U, C) of base-specific RNA fragments.

It is possible to perform the genetic philological information processing such as comparison between the obtained base sequence of the DNA and the base sequence of another DNA which has been already recorded and stored in a suitable means.

The information on the base sequence of DNA determined through the above-described signal processing is output from the signal processing circuit, and subsequently transmitted to a recording device directly or optionally via storage in a storing means such as a magnetic disk or a magnetic tape.

Various recording devices based on various systems can be employed for the above-described purpose, for instance, a device for visualizing optically by scanning a photosensitive material with laser beam, etc., a display means for visualizing electrically on CRT, etc., a means for printing a radiation image displayed on a CRT by means of a video printer, and a means for visualizing on a heatsensitive recording material using thermic rays.

We claim:

1. A signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in a one-dimensional resolving direction on a support medium, which comprises steps of:
(1) detecting at least two bands continuously in the lower part of each resolved row and numbering the bands consecutively in order from the lower end;
(2) obtaining correlation of a distance between the detected bands in the resolving direction with the band's number and predicting positions of undetected bands in the resolving direction from the correlation;
(3) detecting at least one band on the resolved rows on the basis of the predicted positions and numbering the band consecutively;
(4) obtaining the correlation of the distance between the bands with the band's number for the already detected bands including the band newly detected in the step (3), and predicting positions of undetected bands from the correlation; and
(5) repeating in order the steps (3) and (4) to thereby detect all bands on the resolved rows.

2. The signal processing method as claimed in claim 1, wherein said bands are detected by extracting digital signals along the resolving direction of each resolved row and then finding out positions where level of the extracted signal is maximum, in said step (1).

3. The signal processing method as claimed in claim 1, wherein said correlation of the distance between the bands with the band's number is obtained as a regression line or a regression curve, and said positions of undetected bands are predicted by extrapolating the regression line or the regression curve, in said step (2).

4. The signal processing method as claimed in claim 1, wherein said correlation of the distance between the bands with the band's number is obtained for the already detected bands including the band newly detected in the step (3), wherein a band having the lower number is identified and said band having the lower number is excluded in said step (4).

5. The signal processing method as claimed in claim 1, wherein said correlation of the distance between the bands with the band's number is obtained every time detecting a band, and all bands are detected one by one on the resolved rows, in said steps (3) to (5).

6. The signal processing method as claimed in claim 1, wherein said correlation of the distance between the bands with the band's number is obtained every time detecting a given number of bands, and all bands are detected by the given number on the resolved rows, in said steps (3) to (5).

7. The signal processing method as claimed in claim 1, wherein before the step (1), correction for resolved distance is made on each resolved row on the basis of ratio of the resolved distance between the rows, said ratio being determined by detecting inclination of at least one band to the resolving direction for each row.

8. The signal processing method as claimed in claim 1, wherein before the step (1), correction for resolved position is made on each resolved row on the basis of difference in resolved distance between the rows, said difference being determined by detecting at least two bands in the lower part of each row, numbering the bands consecutively in order from the lower end and then obtaining correlation between the band's number and the resolved distance thereof for each row.

9. The signal processing method as claimed in claim 1, wherein the mixture of the base-specific DNA fragments consists of the four groups of:
(1) guanine-specific DNA fragments;
(2) adenine-specific DNA fragments;
(3) thymine-specific DNA fragments; and
(4) cytosine-specific DNA fragments;
and the resolved rows consist of four rows formed by resolving each of said four groups of the base-specific DNA fragments on the support medium.

10. The signal processing method as claimed in claim 1, wherein said digital signals corresponding to the autoradiograph are obtained by placing the support medium and a stimulable phosphor sheet comprising a stimulable phosphor together in layers to record the autoradiograph of the plural resolved rows on the phosphor sheet as an energy-stored image, irradiating said phosphor sheet with stimulating rays and photoelectrically detecting the autoradiograph as stimulated emission.

11. The signal processing method as claimed in claim 1, wherein said digital signals corresponding to the autoradiograph are obtained by placing the support medium and a radiosensitive material together in layers to record the autoradiograph of the plural resolved rows on the radiosensitive material as a visible image and photoelectrically reading out the autoradiograph visualized on said radiosensitive material.

12. A signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in a one-dimensional resolving direction on a support medium, which comprises steps of:
(1) detecting at least two bands continuously in the lower part of each resolved row and numbering the bands consecutively in order from the lower end;
(2) obtaining correlation between a resolved distance of the detected band and the band's number and predicting positions of undetected bands in the resolving direction from the correlation;
(3) detecting at least one band on the resolved rows on the basis of the predicted positions and numbering the band consecutively;
(4) obtaining the correlation of the resolved distance of the band and the band's number for the already detected bands including the band newly detected in the step (3), and predicting positions of undetected bands from the correlation; and
(5) repeating in order the steps (3) and (4) to thereby detect all bands on the resolved rows.

13. The signal processing method as claimed in claim 12, wherein said bands are detected by extracting digital signals along the resolving direction of each resolved row and then finding out positions where level of the extracted signal is maximum, in said step (1).

14. The signal processing method as claimed in claim 12, wherein said correlation of the resolved distance of the band with the band's number is obtained as a regression line or a regression curve, and said positions of undetected bands are predicted by extrapolating the regression line or the regression curve, in said step (2).

15. The signal processing method as claimed in claim 12, wherein said correlation of the resolved distance of the band with the band's number is obtained for the already detected bands including the band newly detected in the step (3) and excluding the band having the lower number, in said step (4).

16. The signal processing method as claimed in claim 12, wherein said correlation of the resolved distance of the band with the band's number is obtained every time detecting a band, and all bands are detected one by one on the resolved rows, in said steps (3) to (5).

17. The signal processing method as claimed in claim 12, wherein said correlation of the resolved distance of the band with the band's number is obtained every time detecting a given number of bands, and all bands are detected by the given number on the resolved rows, in said steps (3) to (5).

18. The signal processing method as claimed in claim 12, wherein before the step (1), correction for resolved distance is made on each resolved row on the basis of ratio of the resolved distance between the rows, said ratio being determined by detecting inclination of at least one band to the resolving direction for each row.

19. The signal processing method as claimed in claim 12, wherein before the step (1), correction for resolved position is made on each resolved row on the basis of difference in resolved distance between the rows, said difference being determined by detecting at least two bands in the lower part of each row, numbering the bands consecutively in order from the lower end and then obtaining correlation between the band's number and the resolved distance thereof for each row.

20. The signal processing method as claimed in claim 12, wherein the mixture of the base-specific DNA fragments consists of the four groups of:
(1) guanine-specific DNA fragments;
(2) adenine-specific DNA fragments;
(3) thymine-specific DNA fragments; and
(4) cytosine-specific DNA fragments;

and the resolved rows consist of four rows formed by resolving each of said four groups of the base-specific DNA fragments on the support medium.

21. The signal processing method as claimed in claim 12, wherein said digital signals corresponding to the autoradiograph are obtained by placing the support medium and a stimulable phosphor sheet comprising a stimulable phosphor together in layers to record the autoradiograph of the plural resolved rows on the phosphor sheet as an energy-stored image, irradiating said phosphor sheet with stimulating rays and photoelectrically detecting the autoradiograph as stimulated emission.

22. The signal processing method as claimed in claim 12, wherein said digital signals corresponding to the autoradiograph are obtained by placing the support medium and a radiosensitive material together in layers to record the autoradiograph of the plural resolved rows on the radiosensitive material as a visible image and photoelectrically reading out the autoradiograph visualized on said radiosensitive material.

23. A signal processing method for determining base sequence of nucleic acids by subjecting digital signals to signal processing, said digital signals corresponding to an autoradiograph of plural resolved rows which are formed by resolving a mixture of base-specific DNA fragments or base-specific RNA fragments labeled with a radioactive element in a one-dimensional resolving direction on a support medium, which comprises steps of:
(1) detecting at least two bands continuously in the lower part of each resolved row and numbering the bands consecutively in order from the lower end;
(2) obtaining correlation of a distance between the detected bands in the resolving direction with the band's number and predicting positions of undetected bands in the resolving direction from the correlation; and
(3) detecting al bands on the resolved rows on the basis of the predicted positions.

24. The signal processing method as claimed in claim 23, wherein said bands are detected by extracting digital signals along the resolving direction of each resolved row and then finding out positions where level of the extracted signal is maximum, in said step (1).

25. The signal processing method as claimed in claim 23, wherein said correlation of the distance between the bands with the band's number is obtained as a regression line or a regression curve, and said positions of undetected bands are predicted by extrapolating the regression line or the regression curve, in said step (2).

26. The signal processing method as claimed in claim 23, wherein said bands are detected by finding out points or areas where signal level is not less than a threshold value and then deciding that the bands exist at the points or areas which correspond to the predicted positions of the undetected bands, in said step (3).

27. The signal processing method as claimed in claim 23, wherein before the step (1), correction for resolved distance is made on each resolved row on the basis of ratio of the resolved distance between the rows, said ratio being determined by detecting inclination of at least one band to the resolving direction for each row.

28. The signal processing method as claimed in claim 23, wherein before the step (1), correction for resolved position is made on each resolved row on the basis of difference in resolved distance between the rows, said difference being determined by detecting at least two bands in the lower part of each row, numbering the bands consecutively in order from the lower end and then obtaining correlation between the band's number and the resolved distance thereof for each row.

29. The signal processing method as claimed in claim 23, wherein the mixture of the base-specific DNA fragments consists of the four groups of:

(1) guanine-specific DNA fragments;
(2) adenine-specific DNA fragments;
(3) thymine-specific DNA fragments; and
(4) cytosine-specific DNA fragments;

and the resolved rows consist of four rows formed by resolving each of said four groups of the base-specific DNA fragments on the support medium.

30. The signal processing method as claimed in claim 23, wherein said digital signals corresponding to the autoradiograph are obtained by placing the support medium and a stimulable phosphor sheet comprising a stimulable phosphor together in layers to record the autoradiograph of the plural resolved rows on the phosphor sheet as an energy-stored image, irradiating said phosphor sheet with stimulating rays and photoelectrically detecting the autoradiograph as stimulated emission.

31. The signal processing method as claimed in claim 23, wherein said digital signals corresponding to the autoradiograph are obtained by placing the support medium and a radiosensitive material together in layers to record the autoradiograph of the plural resolved rows on the radiosensitive material as a visible image and photoelectrically reading out the autoradiograph visualized on said radiosensitive material.

* * * * *